(12) United States Patent
Walton

(10) Patent No.: US 11,207,053 B2
(45) Date of Patent: Dec. 28, 2021

(54) BLOOD VOLUME ASSESSMENT USING HIGH FREQUENCY ULTRASOUND

(71) Applicant: UNIVERSITY OF HAWAII, Honolulu, HI (US)

(72) Inventor: Chad Walton, Honolulu, HI (US)

(73) Assignee: UNIVERSITY OF HAWAII, Honolulu, HI (US)

(*) Notice: Subject to any disclaimer, the term of this patent is extended or adjusted under 35 U.S.C. 154(b) by 976 days.

(21) Appl. No.: 15/765,295

(22) PCT Filed: Aug. 31, 2016

(86) PCT No.: PCT/US2016/049631
§ 371 (c)(1),
(2) Date: Apr. 2, 2018

(87) PCT Pub. No.: WO2017/040612
PCT Pub. Date: Mar. 9, 2017

(65) Prior Publication Data
US 2018/0303459 A1 Oct. 25, 2018

Related U.S. Application Data

(60) Provisional application No. 62/212,236, filed on Aug. 31, 2015.

(51) Int. Cl.
*A61B 8/00* (2006.01)
*A61B 8/08* (2006.01)
*A61B 8/06* (2006.01)

(52) U.S. Cl.
CPC .............. *A61B 8/481* (2013.01); *A61B 8/06* (2013.01); *A61B 8/4488* (2013.01); *A61B 8/488* (2013.01);
(Continued)

(58) Field of Classification Search
CPC .......... A61B 8/481; A61B 8/06; A61B 8/4488
See application file for complete search history.

(56) References Cited

U.S. PATENT DOCUMENTS 5,860,931 A * 1/1999 Chandler ................. A61B 8/06
600/458
2003/0114750 A1 6/2003 Brock-Fisher et al.
(Continued)

OTHER PUBLICATIONS

International Search Report and Written Opinion dated Nov. 8, 2016 for corresponding International Application No. PCT/US2016/049631.
(Continued)

*Primary Examiner* — Joseph M Santos Rodriguez
(74) *Attorney, Agent, or Firm* — Tarolli, Sundheim, Covell & Tummino LLP

(57) ABSTRACT

The present disclosure generally relates to using high frequency ultrasound to assess blood volume changes in a subject. A baseline blood volume value can be determined based on a weight of a subject or based on an initial/previous assessment test value. An image taken with the high frequency ultrasound can be retrieved. A test blood volume value can be measured in a field of view of the image. For example, the test blood volume can be determined based on a destruction/replenishment of a contrast agent during imaging by the high frequency ultrasound. A change in blood volume in the subject can be estimated by comparing the test blood volume value to the baseline blood volume value. The estimate of the change in blood volume can be used to assess a condition of the subject.

8 Claims, 6 Drawing Sheets

(52) U.S. Cl.
CPC .......... *A61B 8/5223* (2013.01); *A61B 8/0883* (2013.01); *A61B 8/0891* (2013.01)

(56) References Cited

U.S. PATENT DOCUMENTS

| | | |
|---|---|---|
| 2005/0049507 A1 | 3/2005 | Clark et al. |
| 2007/0016050 A1 | 1/2007 | Moehring |
| 2008/0177138 A1 | 7/2008 | Courtney |
| 2012/0150003 A1* | 6/2012 | Zhang .................. A61B 5/1455 600/324 |

OTHER PUBLICATIONS

International Preliminary Report on Patentability dated Mar. 6, 2018 for corresponding International Application No. PCT/US2016/049631.

Ross Williams et al., "Dynamic Microbubble Contrast-enhanced US to Measure Tumor Response to Targeted Therapy A Proposed Clinical Protocol with Results from Renal Cell Carcinoma Patients Receiving Antiangiogenic Therapy", Radiology, vol. 260, No. 2, Jan. 1, 2011, pp. 581-590.

J.M Brennan, "Handcarried Ultrasound Measurement of the Inferior Vena Cava for Assessment of Intravascular Volume Status in the Outpatient Hemodialysis Clinic", Clinical Journal of the American Society of Nephrology, vol. 1, No. 4, Jun. 21, 2006, pp. 749-753.

Anonymous: "Estimated Blood Volume Calculator", Medscape, Jul. 29, 2015, http://web.archive.org/web/20150729185711/http://reference.medscape.com/calculator/estimated-blood-volume.

* cited by examiner

BLOOD VOLUME ASSESSMENT USING HIGH FREQUENCY ULTRASOUND

RELATED APPLICATIONS

This application claims the benefit of U.S. Provisional Application No. 62/212,236, entitled "ULTRASOUND MEDIATED ASSESSMENT OF BLOOD VOLUME," filed Aug. 31, 2015. The entirety of this provisional application is hereby incorporated by reference for all purposes.

GOVERNMENT SUPPORT

This invention was made with government support under grant number P30 GM103341 awarded by the National Institutes of Health. The government has certain rights in the invention.

TECHNICAL FIELD

The present disclosure relates generally to blood volume assessment using high frequency ultrasound and, more specifically, to systems and methods for estimating a change in blood volume of a subject based on a high frequency ultrasound image.

BACKGROUND

Accurate estimation of blood volume is essential in patient management, especially in a trauma setting. However, standard techniques for assessing blood volume are impractical for use in a trauma setting, being limited by one or more of the need for specialized equipment, need for specialized teams and operators, radiation exposure, need for central catheterization, need to control patient movement, cost, and time requirements. Accordingly, medical professionals in the trauma setting estimate the blood volume status in emergency patients based on one or more of blood pressure, mental status, heart rate, urine output, and skin condition, leading to inaccurate and unreliable results.

SUMMARY

The present disclosure relates generally to blood volume assessment using high frequency ultrasound and, more specifically, to systems and methods for estimating a change in blood volume of a subject based on a high frequency ultrasound image. High frequency ultrasound can be used in the trauma setting to assess changes in blood volume in emergency patients to provide an accurate and reliable determination of blood loss.

In one aspect, the present disclosure can include a method for using high frequency ultrasound to assess blood volume changes in a subject. The method can include determining, by a system comprising a processor, a baseline blood volume value based on a weight of the subject; retrieving, by the system, an image taken with a high frequency ultrasound; measuring, by the system, based on the image, a test blood volume value in a field of view of the image; and estimating, by the system, a change in blood volume in the subject by comparing the test blood volume value to the baseline blood volume value. The estimate of the change in the blood volume is used to assess a condition of the subject.

In another aspect, the present disclosure can include a system to assess blood volume changes in a subject. The system can include an array of ultrasound transducers to emit high frequency ultrasound waves and acquire an image from a field of view of the subject in response to the high frequency ultrasound waves. The system can also include a computing device comprising a non-transitory memory storing machine executable instructions; and a processor to execute the machine-executable instructions. Upon execution, the machine executable instructions can cause the computing device to control the array of ultrasound transducers to acquire the image; measure a test blood volume value in the field of view based on the image; and estimate a change in blood volume in the subject by comparing the test blood volume value to a baseline blood volume value.

In a further aspect, the present disclosure can include a non-transitory computer readable medium storing instructions that, upon execution, cause a computing device to assess blood volume changes in a subject. The assessment of blood volume can include the following operations: acquiring an image of a field of view of a subject; measuring a test blood volume value in the field of view based on the image; and estimating a change in blood volume in the subject by comparing the test blood volume value to a baseline blood volume value.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
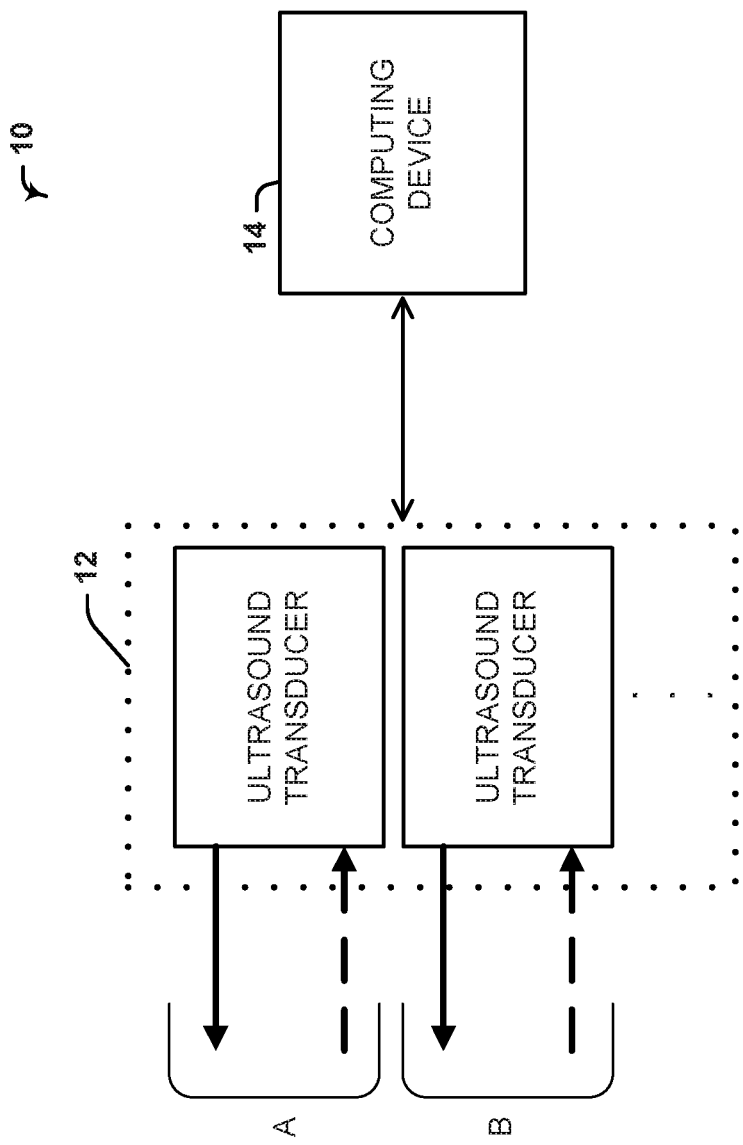
FIG. 1 is a block diagram showing a system that can be used to acquire a high frequency ultrasound image from a subject and estimate a change in blood volume of the subject based on the high frequency ultrasound image in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "blood volume assessment" can refer to the measurement of the volume of blood in a subject's circulatory system (or "volume status"). The blood volume of a subject can be assessed based on an area under a perfusion curve. For example, the perfusion curves can depend on whether the contrast agent is administered as a bolus or administered continuously.

As used herein, the term "ultrasound" can refer to a sonographic imaging technique based on the application of sound waves with frequencies that are higher than those audible to humans. Images are made by sending of pulses of ultrasound into tissue and recording echoes of the sound from the tissue, where different types of tissue echo sound differently.

As used herein, the term "high frequency" can refer to sound waves with a frequency greater than the frequency range of sound waves used in a typical ultrasound. For example, the high frequency can be from 5 MHz to 70 MHz or higher. As another example, the high frequency can be from 15 MHz to 70 MHz or higher. In a further example, the high frequency can be from 20 MHz to 70 MHz or higher.

As used herein, the term ultrasound "transducer" can refer to a device that produces sound waves and receives echoes, which are used to construct an ultrasound image. In some instances, a plurality of ultrasound transducers can be assembled into an array of transducers. The array can be a linear sequential array, a linear phased array, a curved sequential array, a curved phased array, an annular array, or the like.

As used herein, the term "contrast-enhanced ultrasound" or "CEUS" can refer to the application of an ultrasound contrast agent to a traditional ultrasound sonographic imaging technique. In some instances, CEUS can include a high frequency ultrasound.

As used herein, the term "contrast agent" can refer to an internally administered substance that enhances the echo intensity of a blood vessel to increase the ultrasound signal.

As used here, the term "microbubbles" can refer to an ultrasound contrast agent with a gas core surrounded by a lipid shell with a diameter of 1 mm or less. The contents of the gas core and the lipid shell can vary based on the application of the microbubbles.

As used herein, the term "linear contrast" imaging can refer to a visualization of the microbubble contrast agents using B-Mode ultrasound imaging and then applying a reference subtraction algorithm to apply a green contrast overlay on the image to aid in the visualization and quantification of the contrast specific signal.

As used herein, the term "nonlinear contrast" imaging can refer to the use of multiple ultrasound pulses and the nonlinear response of the microbubbles to ultrasound pulses to modulate the intensity of the ultrasound pulses. The goal of this type of imaging is to suppress the tissue signal, while increasing the detection of the contrast agents.

As used herein, the term "power Doppler sonography" can refer to a technique that displays the strength of the Doppler signal in color, rather than the speed and direction information. Power Doppler sonography is more sensitive than conventional color Doppler for detection of flow and is particularly useful for small vessels or vessels with low-velocity flow. In some instances, power Doppler sonography can be used together with linear or nonlinear contrast imaging.

As used herein, the term "focused assessment with sonography for trauma" or "FAST" can refer to a rapid bedside ultrasound that can screen for blood or fluid around the heart or abdominal organs after trauma. The four classic areas that are examined for free fluid are the perihepatic space (also known as Morison's pouch or heptaorenal recess), parasplenic space, pericardium, and the pelvis.

The term "extended FAST" or "eFAST" can refer to the addition of bilateral anterior trunk thoracic areas to the traditional FAST screening areas.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to a rapid and accurate blood volume assessment technique that can be used for trauma patients. Standard techniques for measuring blood volume cannot be used for trauma patients, since these techniques are limited by the need for specialized equipment, need for specialized teams and operators, radiation exposure, need for central catheterization, need to control patient movement, cost, and time requirements. Accordingly, these standard techniques are impractical for use in the trauma setting, where blood volume must be determined urgently and accurately. Therefore, in the trauma setting, a patient's blood volume status is estimated (inaccurately and unreliably) based on one or more of blood pressure, mental status, heart rate, urine output, and skin condition.

Accordingly, the systems and methods of the present disclosure perform an accurate and reliable estimation of a patient's blood volume in a trauma setting using high frequency ultrasound. The estimate can be based on a test blood volume relative to a baseline blood volume determined based on a weight of the patient or based on an initial/previous assessment test value. The test blood volume can be determined based on the area under a perfusion curve determined based on one or more high frequency ultrasound images. Estimating a change in blood volume in this manner is practical for trauma use. For example, the one or more high frequency ultrasound images can be acquired from a specific set of one or more anatomical sites (e.g., FAST sites or eFAST sites) on the patient, which is already done in the trauma setting. The estimate of the change in blood volume obtained using high frequency ultrasound images is more reliable than current estimations of blood volume using one or more of blood pressure, mental status, heart rate, urine output, and skin condition.

III. Systems

One aspect of the present disclosure can include a system 10 (FIG. 1) that can be used to estimate a change in blood volume of a subject based on a high frequency ultrasound image. For example, the high frequency can be from 5 MHz to 70 MHz or higher. As another example, the high frequency can be from 15 MHz to 70 MHz or higher. In a further example, the high frequency can be from 20 MHz to 70 MHz or higher. The frequency of the ultrasound waves can be set based on the size or weight of the subject and a desired depth of penetration. The image is constructed based on a reflected signal with an intensity that varies based on the blood volume.

As an example, the system 10 can employ high frequency ultrasound to estimate changes in blood volume compared to baselines calculated based on a weight of a subject or an initial/previous assessment test value. Notably, the estimate of the change in blood volume obtained using high frequency ultrasound images is more reliable than current estimations of blood volume using one or more of blood pressure, mental status, heart rate, urine output, and skin condition. Additionally, the system 10 can take ultrasound images at sites already used in the trauma setting, facilitating easy clinical adoption. In some instances, one or more of the FAST or eFAST locations can be used for the ultrasound with only the frequency of the ultrasound changing.

The system 10 can include an ultrasound array 12 that can acquire a high frequency ultrasound image from a subject. The ultrasound array 12 can deliver one or more high frequency ultrasound pulses to a field of view of a subject and receive echoes back from elements within the field of view. For example, the elements within the field of view can include one or more blood vessels and/or at least a portion of an organ. A contrast agent can be used to enhance the visualization of the elements. In some instances, the one or more high frequency ultrasound images can be acquired from field of views corresponding to a specific set of one or more anatomical sites (e.g., FAST sites or eFAST sites) on the patient, which is already something done in the trauma setting. For example, the one or more anatomical sites can be on a patient's abdomen.

In some instances, the ultrasound array 12 can be configured as an array with a plurality of transistors. The array can be a linear sequential array, a linear phased array, a curved sequential array, a curved phased array, an annular array, or another type of array. However, in some instances, the linear sequential array or linear phased array is preferred. Each of the plurality of transistors can each transmit one or more ultrasound pulses and receive corresponding echoes (e.g., A and B). In some instances, the ultrasound array 12 can be used for linear contrast imaging, nonlinear contrast imaging, and/or power Doppler imaging. In each case, a contrast agent is delivered to the subject intravenously. The contrast agent can have a high echogeneity compared to surrounding tissue.

A contrast agent can be used for any of linear contrast imaging, nonlinear contrast imaging, and/or power Doppler imaging. The contrast agent can be a microbubble contrast agent, which can be administered intravenously into the subject. Each microbubble can have a gaseous interior and a shell that can be modified for a specific application. The shell can be made of albumin, galactose, lipid, or polymer and may be chosen and/or modified for elasticity. The gas core can be selected based on echogenicity. For example, the microbubble can be non-targeted, having a shell of phospholipid and a core of $C_3F_{10}/N_2$ gas. One example of such a microbubble is the Vevo MicroMarker™ non-targeted contrast agent from FUJIFILM VISUALSONICS.

An example that will be further described is the use of nonlinear contrast ultrasound. In some instances, power Doppler imaging can be used in connection with nonlinear contrast ultrasound. Accordingly, the ultrasound array 12 can be configured for nonlinear contrast imaging, which delivers multiple ultrasound pulses and receives multiple signals illustrating the response of a contrast agent to the multiple ultrasound pulses. In some instances, the ultrasound array 12 can include ultrasound transistors that can be made of a solid-state material (e.g., fabricated using MEMS technology) and coupled to a piezoelectric material or a capacitive material. For example, the solid state material of the ultrasound transducers can be specific for the nonlinear ultrasound imaging.

Figure 2:
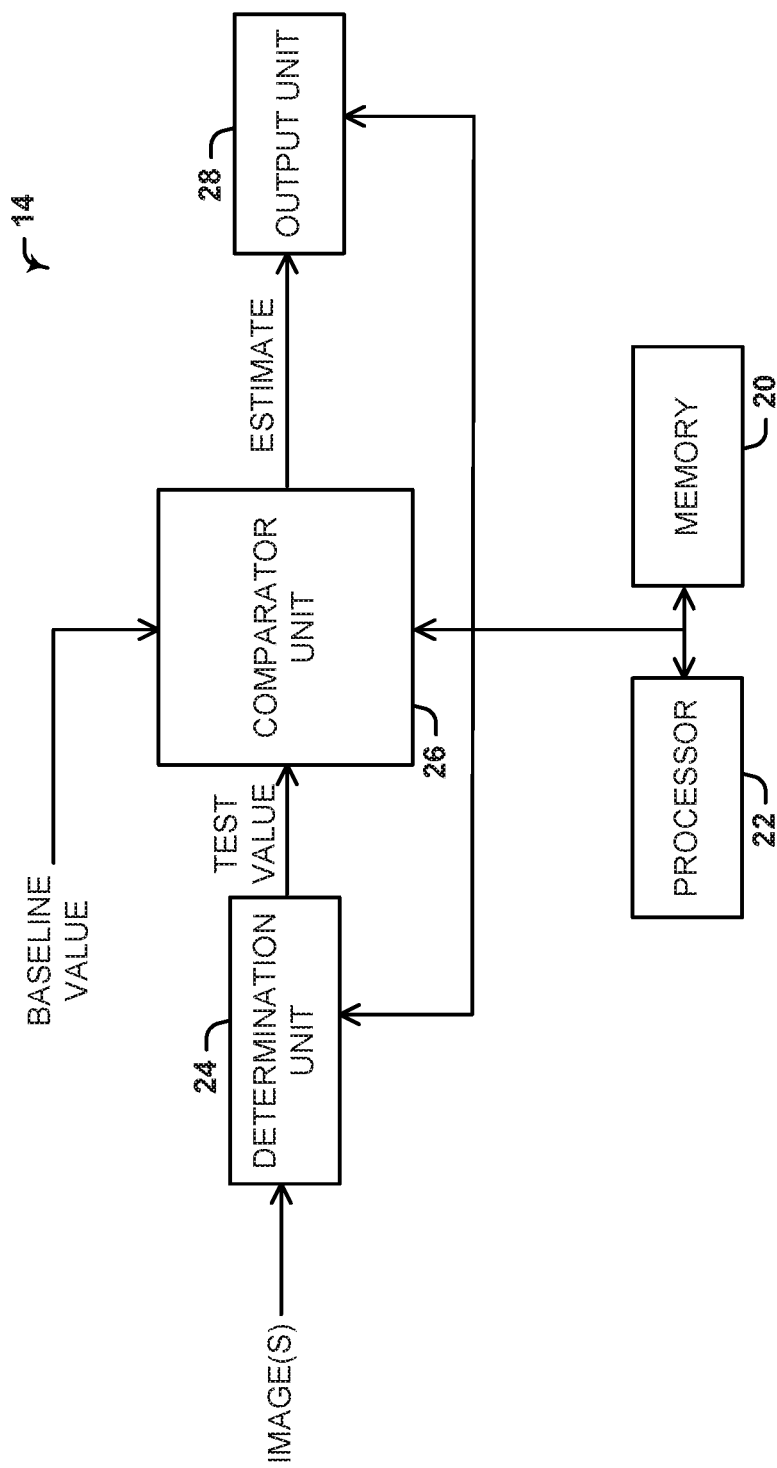
FIG. 2 is a block diagram of an example of the estimation of the change in blood volume of the subject by the computing device in FIG. 1.

A computing device 14 can estimate the change in blood volume of the subject based on the high frequency ultrasound image. The high frequency ultrasound image can be based on the echoes received by the ultrasound array 12. As shown in FIG. 2, the computing device 14 can include a non-transitory memory 20 and a processor 22. The non-transitory memory 20 can be machine readable and store machine-executable instructions, which can be accessed and executed by the processor so that the computing device 14 performs operations. The operations, for example, can be the functionality of the components illustrated in the block diagram. In some instances, the processor 22 can be at least in part a hardware device. Additionally, the non-transitory memory 20 can be a non-transitory computer readable medium (a hardware device).

A determination unit 24 can retrieve the high frequency ultrasound image. For example, the determination unit 24 can retrieve the high frequency ultrasound image from a local storage device (e.g., the non-transitory memory 20). As another example, the determination unit 24 can retrieve the high frequency ultrasound image from a remote storage device (e.g., from a cloud computing platform). As a further example, the image can be provided as detected echoes directly from the ultrasound array 12.

The determination unit 24 can be used to determine a test blood volume value ("test value"). Using a nonlinear contrast image, the test blood value can be calculated according to a bolus perfusion model when the contrast agent is injected as a bolus or a destruction-replenishment perfusion model when the contrast agent is continuously injected. Using the deduction-replenishment perfusion model, microbubbles within the field of view can be destroyed with an acoustic signal and the acoustic signal can be quantified as the field of view is replenished with new microbubbles. The test blood volume can be determined based on the quantified acoustic signal.

In some instances, the determination unit 24 can use the destruction-replenishment perfusion model to measure the test value. Using the destruction-replenishment perfusion model, a high frequency destructive pulse is applied through the ultrasound array 12 into the field of view. The replenishment kinetics are observed in the image over time. The perfusion model is defined as: $f(t) = O + A/2 [1 + \text{erf} \{(\ln(t) - m)/(s\ \text{sqrt}(2))\}]$, where $t > 0$, where O, A, m, and s are fitting parameters and t is time. More specifically, O is the offset, A is an amplitude parameter, and m and s are the mean and standard deviation of the normally distributed natural logarithm of t. The test value can be calculated by plotting f(t) v. t and determining the area under the curve. The area under the curve can be used as the test value that correlates to the blood volume.

Figure 3:
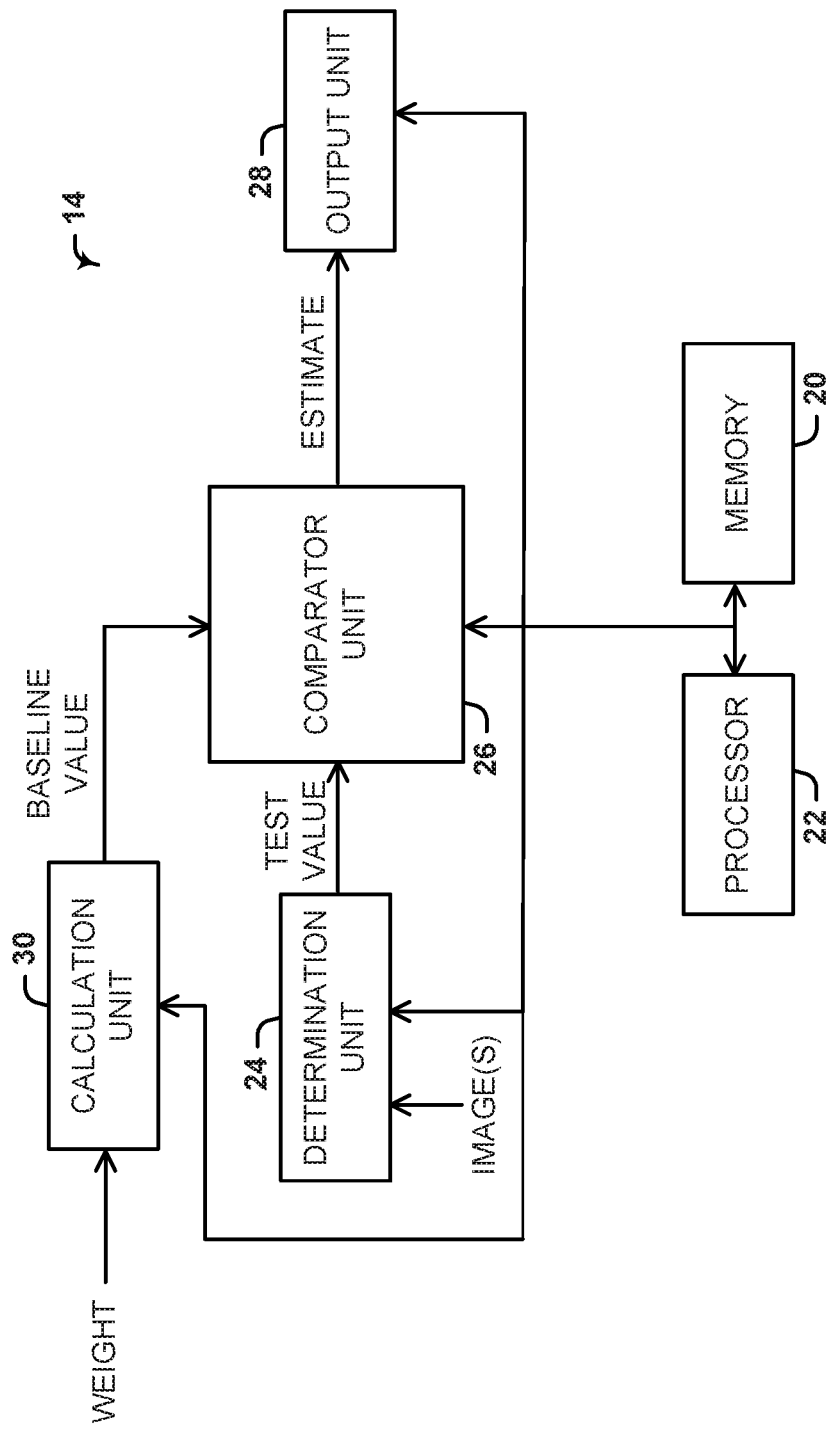
FIG. 3 is a block diagram of an example of the calculation of the baseline value that can be used for the estimation of the change in blood volume of the subject by the computing device in FIG. 1.

The determination unit 24 passes the test value to a comparator unit 26. The comparator unit 26 also receives a baseline value. The baseline value, as shown in FIG. 3, can be calculated by a calculation unit 30 based on a weight of the subject. For example, the calculation unit 30 can access stored values of area under the curve for different weights, and match the closest weight to the subject's weight and use the corresponding area under the curve for the baseline value. In other instances, the baseline value can be an initial/previous assessment test value.

The comparator unit 26 can compare the test value to the baseline value to estimate a change in blood volume in the subject. For example, the comparison can be based on thresholds for losing blood volume, gaining blood volume, and constant blood volume. The thresholds can be determined based on the patient's weight. In other words, the thresholds for an adult male would be different from the thresholds for an infant. The estimate can be sent to an output unit 28, which can output an indication of the estimate in a human perceivable manner. For example, the indication of the estimate can be a graphic and/or an alarm (e.g., with different colors or sounds corresponding to the estimate). The indication can be used by a medical professional to aid in the assessment of a condition of the subject.

The medical professional can take remedial action in response to the indication of the estimate. In some instances, when the estimate indicates that the patient is losing blood volume, the patient can be in shock. Based on change in the blood volume, the class of shock can be determined and appropriate remedial action can be taken. Class I shock is less than 15% blood loss, and minimal treatment is necessary. Class II shock is between 15 and 30% blood loss, and intravenous fluid administration is necessary. Class III shock is between 30 and 40% blood loss, and administration of fluids and packed red blood cells is necessary. Class IV shock is greater than 40% blood loss, and aggressive interventions are necessary. After the resuscitative action is conducted, the accompanying change in blood volume can be reassessed and further remedial action can be taken, if necessary.

IV. Methods

Figure 4:
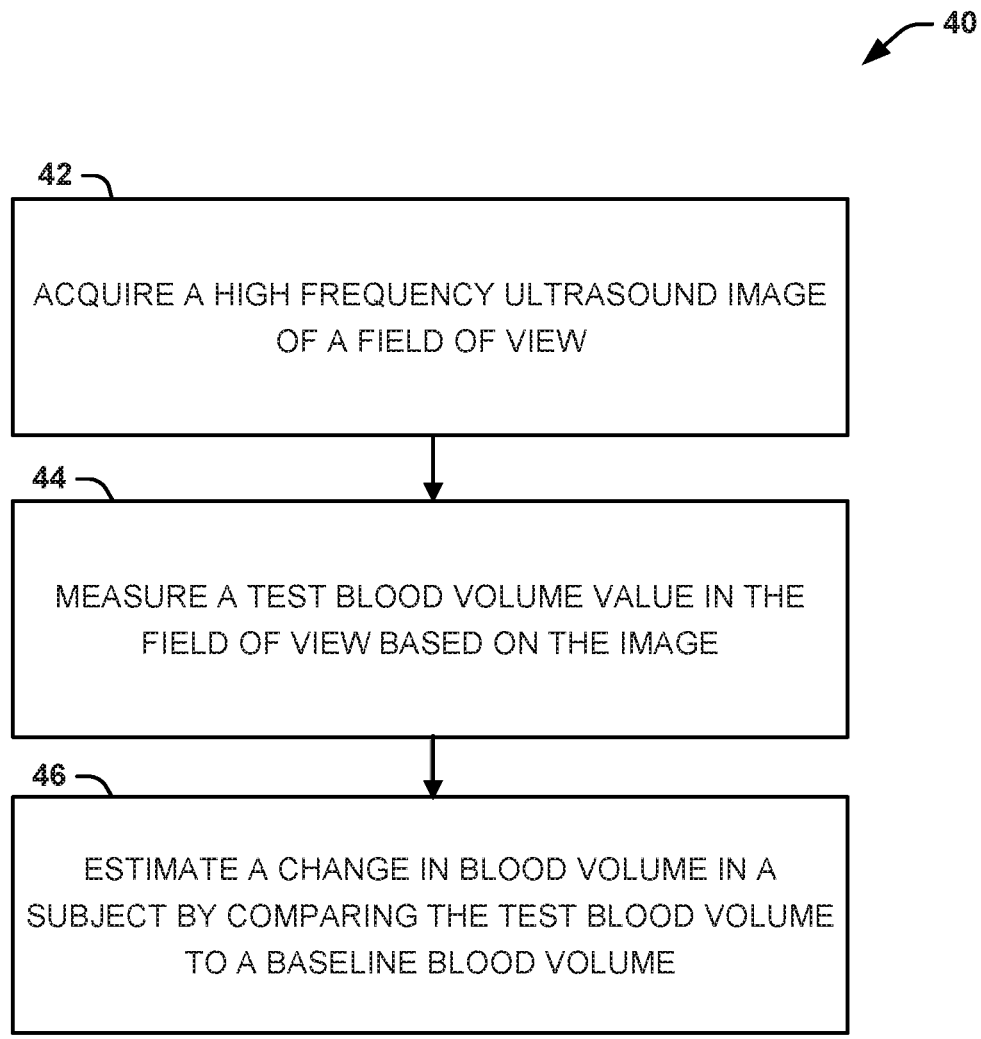
FIG. 4 is a process flow diagram illustrating a method for estimating a change in blood volume of a subject according to another aspect of the present disclosure.

Another aspect of the present disclosure can include methods for estimating a change in blood volume of a subject based on a high frequency ultrasound image. The methods can be implemented (at least in part) by the ultrasound array 12 and the computing device 14 of the system 10 shown in FIG. 1 (and the examples of the computing device 14 shown in FIGS. 2-3). It will be understood that the computing device 14 includes a non-transitory memory 20 and a processor 22. An example of a method 40 for estimating a change in blood volume of a subject is shown in FIG. 4. Additionally, an example of a method 50 for estimating another change in blood volume of the subject after a resuscitative action is performed on the subject is shown in FIG. 5.

Figure 5:
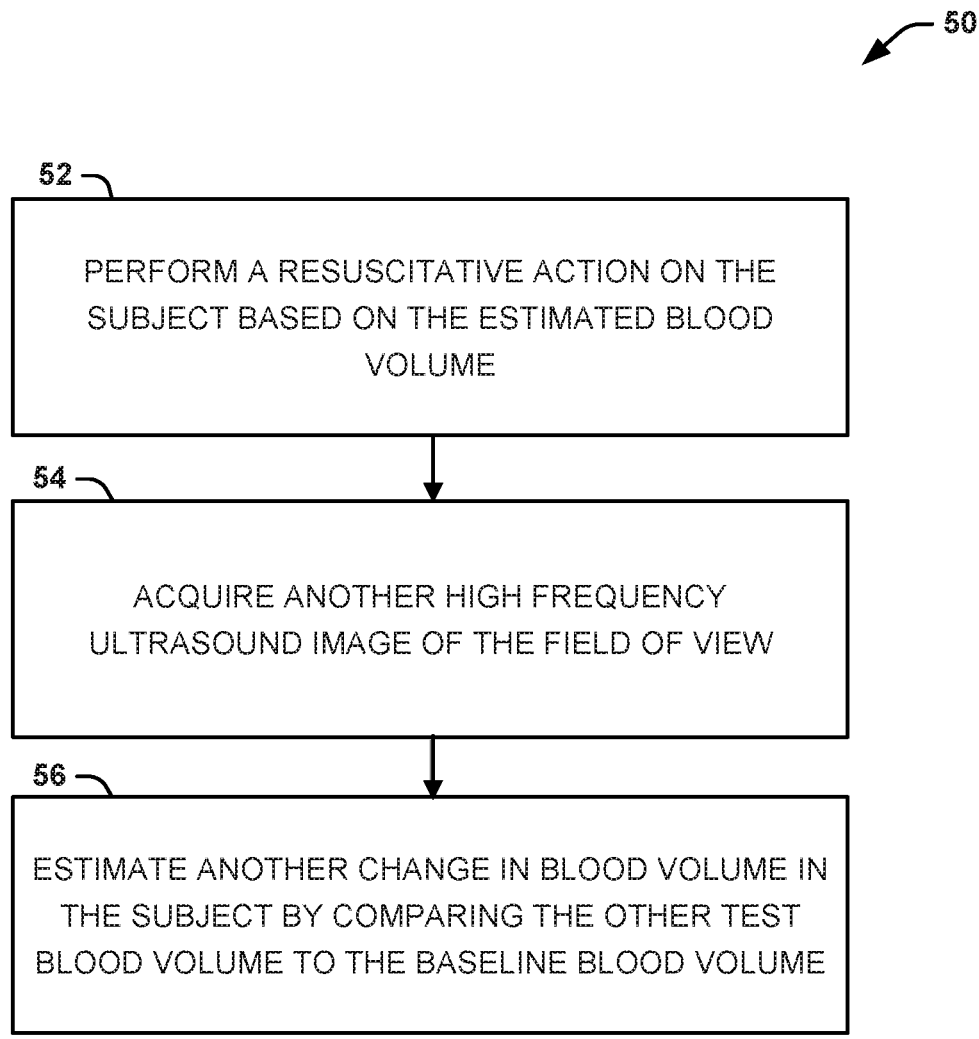
FIG. 5 is a process flow diagram illustrating a method for estimating another change in blood volume of the subject after a resuscitative action is performed on the subject according to another aspect of the present disclosure.

The methods 40 and 50 of FIGS. 4 and 5, respectively, are illustrated as process flow diagrams with flowchart illustrations. For purposes of simplicity, the methods 40 and 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40 and 50.

Referring now to FIG. 4, illustrated is a method 40 for estimating a change in blood volume of a subject. At 42, a high frequency ultrasound image can be acquired of a field of view. At 44, a test blood volume value in the field of view can be measured based on the image. For example, the image can be recorded according to a destruction-replenishment perfusion model, and the test blood volume value can be related to an area under the curve of a perfusion model. A baseline blood volume can be calculated or otherwise retrieved based on the subject's weight or based on an initial/previous assessment test value. At 46, a change in the blood volume in the subject can be estimated by comparing the test blood volume to the baseline blood volume. An indication of the change can be output, and remedial measures can be taken to assist the subject based on the estimated change in blood volume. For example, when the estimate indicates that the patient is losing blood volume, the patient can be in shock. Class I shock is less than 15% blood loss, and minimal treatment is necessary. Class II shock is between 15 and 30% blood loss, and intravenous fluid administration is necessary. Class III shock is between 30 and 40% blood loss, and administration of fluids and packed red blood cells is necessary. Class IV shock is greater than 40% blood loss, and aggressive interventions are necessary.

Illustrated in FIG. 5 is a method 50 for estimating another change in blood volume of the subject after a resuscitative action is performed on the subject. At 52, the resuscitative action is performed on the subject based on the estimated blood volume. At 54, another high frequency ultrasound image is acquired from the field of view. At 56, another change in the blood volume can be estimated by comparing the other test blood volume to the baseline blood volume. Based on this estimate, additional resuscitative action may be taken.

V. Experimental

The following experiment shows that contrast enhanced ultrasound (CEUS) can be used for an accurate measurement of blood volume during blood loss and resuscitation. The results show that CEUS is feasible using abdominal windows similar to FAST.

Methods

A combination of nonlinear contrast and power Doppler imaging was employed using a destruction-replenishment protocol to measure blood volume in mice. Animal protocols were approved by University of Hawaii IACUC.

Animals

All male, inbred mouse strain (C57bl/6j) were used.

Anesthesia

The mice were anesthetized by 2.5% isoflurane induction with 1.5% maintenance. Mice were shaved and depilated to facilitate ultrasound imaging. Mice were placed on an ultrasound stereotaxis control and telemetry table attached to a VEVO 2100 ultrasound machine (FujiFilm, Montreal, Canada). The telemetry table recorded physiology (EKG, HR, body temp), while warming the animal to 37° C. Pulse rate, breath depth and frequency, toe pinch, and respiration rate were monitored intra-operatively. Mice were also continually monitored on an EKG, heart rate, breath rate and temperature recording surgical table that also maintained a 37° C. temperature.

Carotid Catherization

Surgical areas were scrubbed with iodine scrub for sterility and draped in standard manner. A 1-2 cm midline neck incision from just below the mandible to the thoracic inlet wall was made. Under a dissecting microscope, the right carotid artery was exposed and carefully separated from other neighboring structures including the vagus nerve. Once the carotid artery had been isolated, a silk suture (7-0 or 6-0) was placed distally (closer to the head) for the complete ligation of the vessel. A second silk suture was placed proximally (closer to the heart) to allow temporary obstruction of blood flow. Finally, a third silk suture was placed loosely between the first two ligatures and a small incision (arteriotomy) was made distal to the middle ligature. The tip of a catheter, which had been pre-filled with 10-30% heparinized saline, was placed in the incision area, of the carotid artery and secured in place by tying the mid (i.e., the third) suture once that catheter had been advanced past the ligature. The proximal ligature was released and re-ligated after the catheter had been advanced for about 1-3 mm. This allowed for easy blood withdrawals.

Power Doppler and Nonlinear Contrast Imaging

Mice were infused with $0.5 \times 10^7$ microbubbles per 25 µl injection of microbubbles (unconjugated MicroMarker™ contrast agent, FujiFilm) via 31G tail vein injection. Using nonlinear contrast imaging mode and power Doppler imaging (using a MS 250 transducer with a frequency range of 13-24 MHz), the bubbles were recorded entering the target area, destroyed and imaged returning into the target region, creating a "wash-in versus wash-out" image. The first injection of contrast served as the baseline. Images were taken for each target area (Diaphragmatico-hepatic [DH], Spleno-renal [SR], Cysto-colic [CC], and Hepato-renal [HR]).

Blood Volume Removal 20 minutes following baseline imaging, 20% total circulating blood volume was removed via carotid artery catheter and re-imaging performed for all animals.

Confirmation of Level II Shock

Level II shock is categorized by a 15-30% blood loss and results in tachycardia and low blood pressure. Since pressure catheters were not used, tachycardia was observed via EKG monitoring as the indication of level II shock. The test animals had a baseline heart rate (HR) of 470 beats per minute (BPM), with a range of 421-532 and demonstrated an increase to an average of 545 BPM, with a range of 510-611 BPM.

Resuscitation 20 minutes after the blood draw, re-injection and injection subsequent ultrasound analyses, 20% of the original total blood volume was replaced with sterile saline (PBS, Sigma-Aldrich), bringing the animals back to volume baseline (or resuscitated). Resuscitation was considered to be achieved by the restoration of normal heart rate in the animals via EKG monitoring. Ultrasound imaging was conducted as previously described after re-injection of the contrast agent.

Euthanize

Mice were euthanized via anesthesia overdose (isofurane concentration of 5% until one minute after breathing stopped) at the conclusion of the ultrasound imaging.

Analysis with VEVO-CQ

Figure 6:
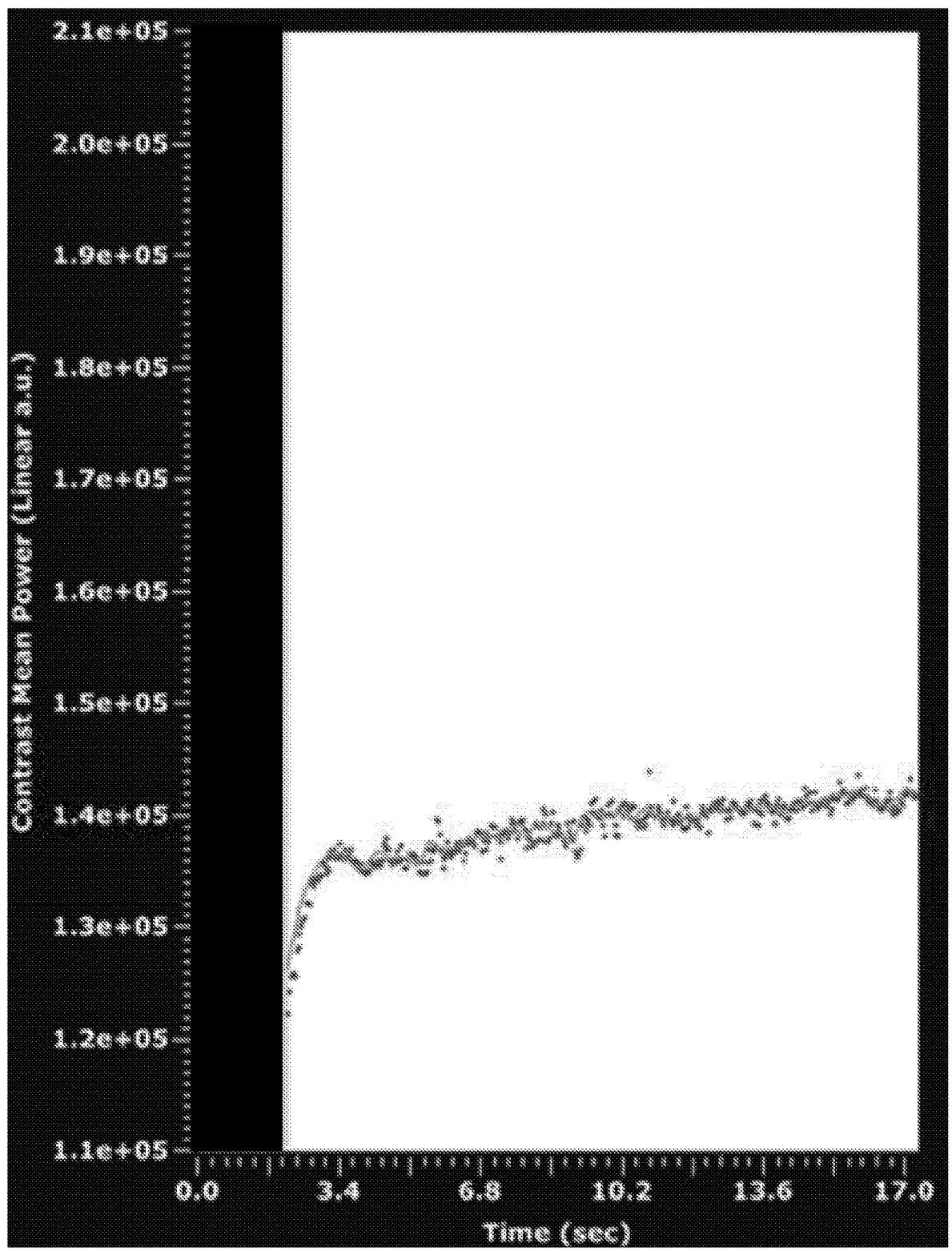
FIG. 6 shows an example of a perfusion curve obtained from the Diaphragmatico-Hepatic region of interest that can be used to estimate the blood volume.

VEVO-CQ software was used to quantify the "wash-in/wash-out" data and calculate the area under the replenishment curve (AUC) measurements for baseline, blood loss, and resuscitated for each ultrasound site. This gave a complete picture of the blood volume in the target organ and surrounding area (an example of the perfusion curve obtained for the DH field of view, for which the area under the curve can be calculated, is shown in FIG. 6).

Statistical Analysis

Correlations between blood volume status and area under the curve (AUC) were analyzed using Pearson correlation coefficient (r) for each ultrasound site, and using partial correlation coefficient controlling for ultrasound site. A P value of less than 0.05 was considered statistically significant.

Results

The calculated circulating blood volume (CCBV) significantly correlated with area under the replenishment curve (AUC) baseline measurement, AUC blood loss measurement and AUC resuscitated measurement for each ultrasound site (shown in Table 1).

TABLE 1

Averaged raw data for area under the curve for nonlinear contrast analysis.

| Ultrasound site | Area Under the Curve (AUC) Baseline measurement (a.u.) | Area Under the Curve (AUC) Blood loss measurement (a.u.) | % compared to baseline | Area Under the Curve (AUC) Resuscitated measurements (a.u.) | % compared to baseline |
|---|---|---|---|---|---|
| DH | 1.21-1.75 (Mean = 1.36) | 1.06-1.53 (Mean = 1.17) | 84-90 (Mean = 86) | 1.19-1.68 (Mean = 1.34) | 96-98 (Mean = 98) |
| SR | 1.23-1.83 (Mean = 1.44) | 1.1-1.61 (Mean = 1.24) | 71-91 (Mean = 86) | 1.21-1.83 (Mean = 1.41) | 95-100 (Mean = 98) |
| CC | 0.58-1.1 (Mean = 0.65) | 0.51-0.94 (Mean = 0.55) | 79-90 (Mean = 85) | 0.55-0.93 (Mean = 0.62) | 85-96 (Mean = 95) |
| HR | 1.28-1.93 (Mean = 1.48) | 1.11-1.74 (Mean = 1.33) | 88-91 (Mean = 90) | 1.23-1.85 (Mean = 1.44) | 93-99 (Mean = 97) |
|  | n = 13 | n = 13 |  | n = 10 |  |

Circulating blood volume (mL) adjusted by weight
0.87-1.24 (mean = 1.04)
% Total blood volume removed*
18.1-22.9 (mean = 20.0)
Diaphragmatico-hepatic [DH], Spleno-renal [SR], Cysto-colic [CC], and Hepato-renal [HR])
Fitted curve Quality of Fit (QOF) cut off 90% for each ROI
*Equal amont resuscitated The total blood volume loss (TBVL) and AUC blood loss measurement were not significantly correlated for each ultrasound site. When controlled for ultrasound site, the CCBV showed a high positive correlation with AUC baseline measurement (partial correlation coefficient=0.83, p<0.001), a moderately positive correlation with AUC blood volume loss measurement (partial correlation coefficient=0.69, p<0.001) and a high positive correlation with AUC resuscitated measurement (partial correlation coefficient=0.80, p<0.001). TBVL showed a low negative correlation with AUC blood loss measurement (partial correlation coefficient=−0.35, p=0.013). The correlations are shown in Table 2. Power Doppler studies did not produce any significant results due mostly to the difficulty in using this technique in a rapid manner. It may prove more useful in larger animals or more advanced levels of shock.

TABLE 2

Partial correlation controlling for all ultrasound sites.

| Variables | Partial Correlation | p-value |
|---|---|---|
| Calculated Circulating Blood Volume (CCBV) and AUC Baseline Measurement | 0.8330 | <.0001 |
| Total Blood Volume Loss (TBVL) (%) and AUC Blood Loss Measurement | −0.352 | 0.0130 |
| Calculated Circulating Blood Volume (CCBV) and AUC Blood Loss Measurement | 0.6947 | <.0001 |
| Calculated Circulating Blood Volume (CCBV) and AUC Resuscitated Measurement | 0.8040 | <.0001 |

From the above description, those skilled in the art will perceive improvements, changes and modifications. Such The following is claimed:

1. A system comprising:
an array of ultrasound transducers to emit a high frequency sound waves and acquire one or more images from each of a set of anatomical sites on a subject's abdomen within a field of view of the subject in response to the high frequency sound waves; and
a computing device, comprising:
a non-transitory memory storing machine executable instructions; and
a processor to execute the machine-executable instructions to:
control the array of ultrasound transducers to acquire the one or more images from each of the set of anatomical sites;
calculate, based on the one or more images for each of the set of anatomical sites on the subject and a perfusion model based on injection of a contrast agent, test blood volume values for each of the set of anatomical sites; and
estimate a change in blood volume in the subject by comparing the test blood volume values for each of the set of anatomical sites to a baseline blood volume value for each of the set of anatomical sites,
wherein an alert to take a remedial action is given when the estimate of the change in blood volume is greater than a threshold for at least one of the set of anatomical sites.

2. The system of claim 1, wherein the processor further executes the machine-executable instructions to determine the baseline blood volume value for each of the set of anatomical sites based on a weight of the subject.

3. The system of claim 1, wherein the one or more images are acquired at a frequency set based on a weight of the subject and a depth of penetration.

4. The system of claim 1, wherein the one or more images are acquired upon administration of a concentration of microbubbles to the subject to act as the contrast agent.

5. The system of claim 4, wherein the perfusion model is based on a contrast destruction/replenishment protocol, the contrast destruction/replenishment protocol comprising:
destroying microbubbles in the field of view with the high frequency sound waves;
quantifying an acoustic signal as the field of view is replenished with new microbubbles; and
determining the test blood volume based on the quantified acoustic signal.

6. The system of claim 1, wherein the array of ultrasound transducers is an array of solid-state ultrasound transducers.

7. The system of claim 6, wherein the array of solid-state ultrasound transducers are specific for nonlinear contrast imaging as a continuous infusion of microbubbles is administered to the subject.

8. The system of claim 1, wherein the system is configured to repeat the estimate for a new image at a later time.

* * * * *